US00PP34568P2

(12) United States Plant Patent
Berry

(10) Patent No.: US PP34,568 P2
(45) Date of Patent: Sep. 13, 2022

(54) ***HIBISCUS* PLANT NAMED 'JBG AH-09'**

(50) Latin Name: *Hisbiscus rosa-sinensis*
Varietal Denomination: JBG AH-09

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/576,418

(22) Filed: Jan. 14, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

(56) References Cited

U.S. PATENT DOCUMENTS

PP6,473 P * 12/1988 Zamora ..... Plt./257

OTHER PUBLICATIONS

Hollywood *Hibiscus*, retrieved on Mar. 3, 2022, retrieved from the Internet at https://www.hollywoodhibiscus.com/personalities, 11 pp. (Year: 2022).*

Mobilian, J. Berry announces new 2021 varieties, Greenhouse Management posted on Jul. 21, 2020, retrieved on Mar. 3, 2022, retrieved from the Internet at https://www.greenhousemag.com/article/j-berry-announces-2021-varieties/, 6 pp. (Year: 2020).*

Monrovia for Bridal Veil *Hibiscus*, retrieved on May 19, 2022 at https://www.monrovia.com/bridal-veil-hibiscus.html, 4 pp. (Year: 2022).*

* cited by examiner

*Primary Examiner* — June Hwu
(74) *Attorney, Agent, or Firm* — The Webb Law Firm

(57) ABSTRACT

A new and distinct *Hibiscus* plant having dark green colored leaves and large, white colored flowers that last for several days on the plant.

2 Drawing Sheets

Botanical classification: *Hibiscus rosa-sinensis.*
Varietal denomination: 'JBG AH-09'.

BACKGROUND OF THE INVENTION

The present invention comprises a new and distinct *Hibiscus* plant having the varietal name 'JBG AH-09'. The new variety is the result of a planned breeding program with the purposes of developing *Hibiscus rosa-sinensis* plants that exhibit whitefly and leaf spot resistance, propagation and production efficiencies, durable and exotic flowers, and abundant flowering. 'JBG AH-09' is the result of a cross conducted in Grand Saline, Tex. between *Hibiscus rosa-sinensis* varieties 'JBG 15005' (female parent, unpatented) and 'JBG 14006' (male parent, U.S. Plant Pat. No. 30,597). The new variety was selected in February of 2016 in Grand Saline, Tex. and the first asexual reproduction of the new variety was conducted by semi-hardwood cuttings in June of 2016 in Grand Saline, Tex. 'JBG AH-09' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG AH-09' is similar to its female parent in having a mainly white flower color with temperature sensitive pink blushing on the petals. 'JBG AH-09' differs from its female parent in that the new variety exhibits much thicker, greener, and bigger leaves. Further, the flowers of 'JBG AH-09' are more durable than its female parent—lasting from 2-3 days versus 1 day. 'JBG AH-09' is similar to its male parent in leaf shape, alternate leaf arrangement, and upright growth habit. 'JBG AH-09' differs from its male parent in flower color (white versus red), exhibiting more branching, larger flowers, and more vigorous growth.

When 'JBG AH-09' is compared to *Hibiscus rosa-sinensis* variety 'Starstruck' (unpatented), both varieties have mainly white colored flowers and leaf spot pathogen resistance. However, 'JBG AH-09' has much darker colored foliage and a more coarse growth habit as compared to the mounding habit with finer branching of 'Starstruck'.

The following traits distinguish 'JBG AH-09' as a new and distinct cultivar from other *Hibiscus* varieties known to the breeder:

1. Thick and dark green colored leaves with a leathery touch;
2. Saturated white flower color;
3. Large flower size;
4. Coarse rooting habit; and
5. Stiff, thick, and durable flower petals.

DESCRIPTION OF THE DRAWINGS

The accompanying photographic images illustrate the new variety at approximately four months of age, with the colors being as nearly true as is possible with color illustrations of this type.

DESCRIPTION OF THE PLANT

Figure 1:
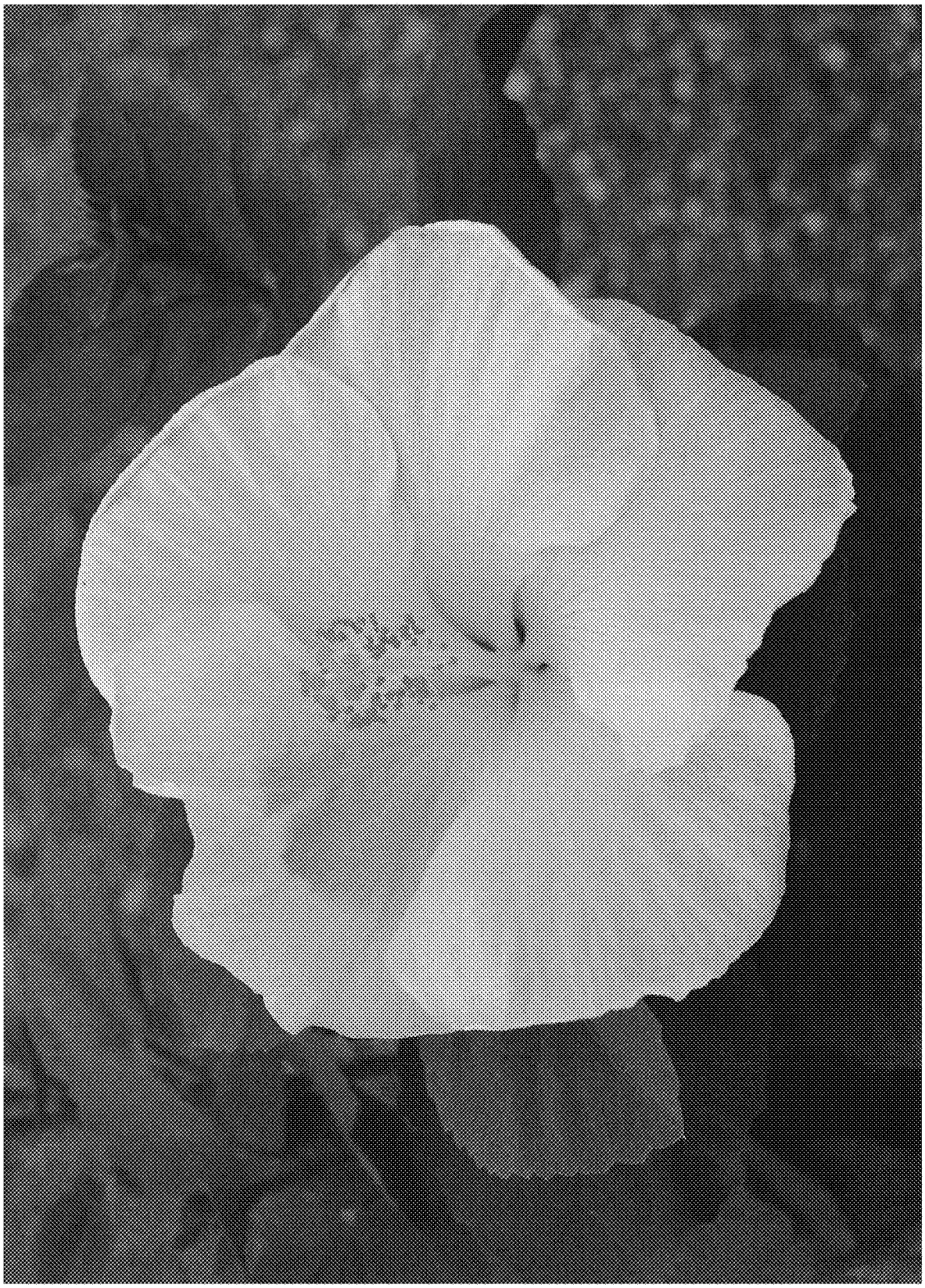
FIG. 1 illustrates a close-up view of a flower of the new variety.
Figure 2:
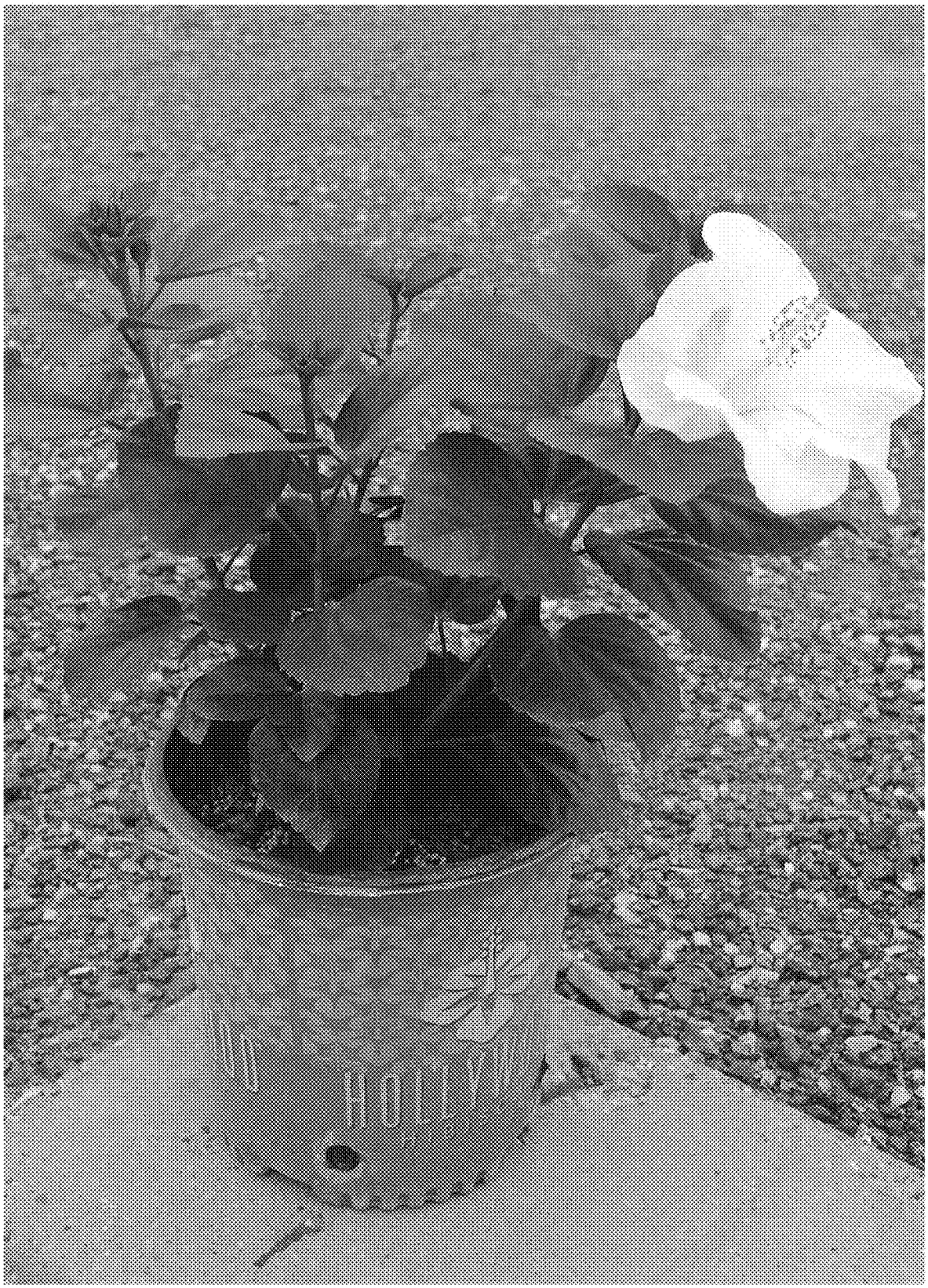
FIG. 2 illustrates a close-up view of an entire plant of the new variety.

The following detailed description sets forth the characteristics of the new variety. The plants were grown in greenhouse heated to a minimum of approximately 13° C. during the cool season, which is otherwise kept at ambient temperatures with a light shade of about 30% in the hot season. The color readings and measurements were taken indoors in Grand Saline, Tex. under fluorescent lighting near natural window light on approximately four month old plants that were grown in 2 gallon containers. Color references are primarily to The 1995 R.H.S. Colour Chart of The Royal Horticultural Society of London, 3$^{rd}$ Edition, except where general color terms are used.

PLANT

Time to initiate roots: About 12 days at an average of 24° C.

Time to develop roots: About 50 days at an average of 21-24° C.

Time to produce a finished flowering plant from a rooted cutting: About 12-16 weeks in a 1 gallon/20.0 cm diameter container.

Specific disease/pest resistance: Resistance to whitefly (*Trialeurodes vaporariorum*) and bacterial leaf spot (*Pseudomonas* spp.).

Heat/cold tolerance: Thrives above 24° C., but expires at temperatures of 0° C. and below.

Drought tolerance: Moderate to none.

Plant:

- *Type*.—Tropical, ornamental shrub.
- *Habit*.—Upright; freely branching.
- *Height*.—35.6 cm from the top of the pot.
- *Spread*.—45.7 cm.
- *Vigor*.—High.
- *Rooting*.—Coarse and well-branched.

Stem:

- *Number per plant*.—18.
- *Length*.—Ranging from 30.5-35.0 cm.
- *Width*.—0.6 cm.
- *Texture*.—Immature: Slightly textured, only prominent veins can be felt. Mature: Thick, durable, and smooth.
- *Strength*.—Strong.
- *Branch number*.—Approximately 14 per stem.
- *Internode length*.—2.5-3.8 cm.
- *Color*.—Immature: 143B. Mature: 143A.
- *Stipules*.—Number per node: 2. Shape: Spinose. Length: 1.0 cm. Width: 1.0 mm. Surface texture: Smooth. Apex: Acute. Base: Linear. Margin: Entire. Color: 143A.

Foliage:

- *Arrangement*.—Alternate.
- *Size of leaf*.—Length: Approximately 11.0 cm. Width: Approximately 11.0 cm.
- *Shape of leaf* (*generally*).—Ovate.
- *Shape of apex*.—Acute.
- *Shape of base*.—Rounded.
- *Texture*.—Upper surface: Smooth and waxy with a little vein texture. Lower surface: Smooth and heavily textured from veins.
- *Margin type*.—Crenate.
- *Color*.—Young leaves: Upper surface: 139A. Lower surface: 137A. Mature leaves: Upper surface: 147A. Lower surface: 137C.
- *Veins*.—Venation type: Palmate. Color: Upper surface: 139A. Lower surface: 137C.
- *Petiole*.—Length: 3.8 cm. Diameter: 3.0 mm. Texture: Slightly textured. Color: 137C.

FLOWERS

Buds (described approximately two days before opening):

- *Shape*.—Elliptical.
- *Diameter*.—2.2 cm.
- *Length*.—5.1 cm.
- *Color*.—137C.

Natural flowering season: Year round in Grand Saline, Tex.

Flower type and habit: Single, with slightly overlapping petals.

Fragrance: None observed.

Flowers:

- *Number per stem*.—1.
- *Overall depth*.—1.9 cm.
- *Overall diameter*.—16.5 cm.
- *Shape*.—Rotate.
- *Lastingness*.—2-3 days on the plant.
- *Petals*.—Number: 5. Arrangement: Simple. Length: 10.8 cm. Width: 10.2 cm. Shape: Ovate. Apex: Obtuse, with weak incisions. Base: Acute. Margin: Entire, with weak undulation intensity. Texture/appearance: Upper surface: Very smooth. Lower surface: Slightly textured from the veins. Color: When opening: Upper surface: 155D. Lower surface: 155A. Fully opened: Upper surface: 155C. Lower surface: 155A.
- *Calyx*.—Form: Fused. Overall length: 3.0 cm. Overall diameter: 2.2 cm. Sepals/calyx lobes: Number: 5. Shape: Lanceolate. Apex: Acute. Margin: Entire. Texture: Smooth inner surface and the outer surface is slightly textured from tiny bumps/hair-like extensions. Color: Outer surface: 143B. Inner surface: 144A.
- *Epicalyx*.—Length: 1.5 cm. Width: 2.4 cm. Texture: Mostly smooth. Color: 153A.
- *Bracts*.—Not present (see epicalyx).
- *Peduncle*.—Length: 1.0 cm. Diameter: 4.0 mm. Strength: Stiff and firm. Angle: Acute. Texture: Smooth. Color: 143B.

Reproductive organs:

- *Gynoecium*.—Pistils: Number: 1. Length: 10.5 cm. Stigma: Number: 5. Shape: Round. Length: 5.0 mm. Diameter: 3.0 mm. Color: 21A. Style: Length: 8.3 cm. Width: 5.0 mm. Color: 155D. Ovary: Shape: Ovate. Length: 15.0 mm. Width: 12.0 mm. Color: 155D.
- *Androecium*.—Stamens: Number: 97. Position: Just below the stigma on the style. Anther: Shape:

U-shaped. Diameter: 1.0 mm. Color: 23B. Filament: Length: 8.0 mm. Width: 1.0 mm. Color: 155B. Pollen: Color: 23A. Amount (generally): Low to moderate.

SEEDS

Seeds:

*Number.*—4.

*Color.*—200A.

*Length.*—4.0 mm.

*Width.*—2.0 mm.

The invention claimed is:

1. A new and distinct variety of *Hibiscus* plant named 'JBG AH-09', substantially as illustrated and described herein.

* * * * *